United States Patent
Bentwich et al.

(10) Patent No.: US 9,624,556 B2
(45) Date of Patent: Apr. 18, 2017

(54) VIRAL AND VIRAL ASSOCIATED MIRNAS AND USES THEREOF

(71) Applicant: Rosetta Genomics Ltd., Rehovot (IL)

(72) Inventors: Itzhak Bentwich, Misgav (IL); Amir Avniel, Tel Aviv (IL); Yael Karov, Tel Aviv (IL); Ranit Aharonov, Tel Aviv (IL)

(73) Assignee: Rosetta Genomics Ltd., Rehovot (IL)

( * ) Notice: Subject to any disclaimer, the term of this patent is extended or adjusted under 35 U.S.C. 154(b) by 0 days.

(21) Appl. No.: 14/797,381

(22) Filed: Jul. 13, 2015

(65) Prior Publication Data

US 2016/0047004 A1    Feb. 18, 2016

Related U.S. Application Data

(60) Division of application No. 13/887,506, filed on May 6, 2013, now abandoned, which is a division of application No. 12/850,091, filed on Aug. 4, 2010, now Pat. No. 8,455,633, which is a division of application No. 11/511,035, filed on Aug. 28, 2006, now Pat. No. 7,795,419, which is a continuation-in-part of application No. PCT/IB2005/002352, filed on May 26, 2005, which is a continuation-in-part of application No. 10/709,739, filed on May 26, 2004, now Pat. No. 7,777,022.

(60) Provisional application No. 60/522,459, filed on Oct. 4, 2004, provisional application No. 60/665,094, filed on Mar. 25, 2005, provisional application No. 60/522,450, filed on Oct. 3, 2004, provisional application No. 60/522,451, filed on Oct. 3, 2004.

(51) Int. Cl.
| | | |
|---|---|---|
| C07H 21/04 | (2006.01) | |
| C07H 21/02 | (2006.01) | |
| C12N 15/00 | (2006.01) | |
| C12Q 1/70 | (2006.01) | |
| C12N 15/11 | (2006.01) | |
| C12N 15/113 | (2010.01) | |

(52) U.S. Cl.
CPC ............ *C12Q 1/701* (2013.01); *C12N 15/111* (2013.01); *C12N 15/1131* (2013.01); *C12N 2310/14* (2013.01); *C12N 2310/141* (2013.01); *C12N 2320/10* (2013.01); *C12N 2320/30* (2013.01); *C12N 2330/10* (2013.01); *C12N 2710/16222* (2013.01); *C12Q 2600/136* (2013.01)

(58) Field of Classification Search
None
See application file for complete search history.

(56) References Cited

U.S. PATENT DOCUMENTS 6,582,908 B2 *  6/2003  Fodor .................. B01J 19/0046
                                                        435/288.3

OTHER PUBLICATIONS

GenBank AI009835 (1999).*
Tang et al (Journal of Virology, Feb. 2009, p. 1433-1442 vol. 83, No. 3).*

* cited by examiner

*Primary Examiner* — Richard Schnizer
(74) *Attorney, Agent, or Firm* — Polsinelli PC; Ron Galant

(57) ABSTRACT

Described herein are novel polynucleotides associated with viral infections. The polynucleotides are miRNAs and miRNA precursors. Related methods and compositions that can be used for diagnosis, prognosis, and treatment of those medical conditions are disclosed. Also described herein are methods that can be used to identify modulators of viral infections.

6 Claims, 6 Drawing Sheets

FIG. 2A

5'UTR SEQUENCE (5' TO 3') OF HIV-1 (U5-R)

GGTCTCTCTGGTTAGACCAGATCTGAGCCTGGGAGCTCTCTGGCTAACT
AGGGAACCCACTGCTTAAGCCTCAATAAAGCTTGCCTTGAGTGCTTCAAGTA
GTGTGTGCCCGTCTGTTGTGTGACTCTGGTAACTAGAGATCCCTCAGACCCTT
TTAGTCAGTGTGGAAAATCTCTAGCAGTGGCGCCCGAACAGGGACCTGAAAG
CGAAAGGGAAACCAGAGGAGCTCTCTCGACGCAGGACTCGGCTTGCTGAA
GCGCGCACGGCAAGAGGCGAGGGGCGGCGACTGGTGAGTACGCCAAAAA
TTTTGACTAGCGGAGGCTAGAAGGAGAGAG

FIG. 2B

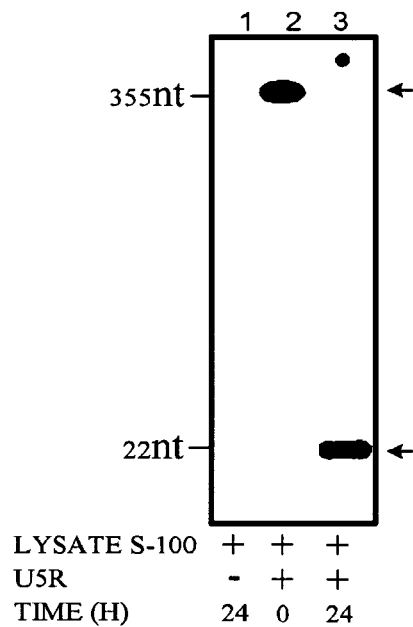

FIG. 2C

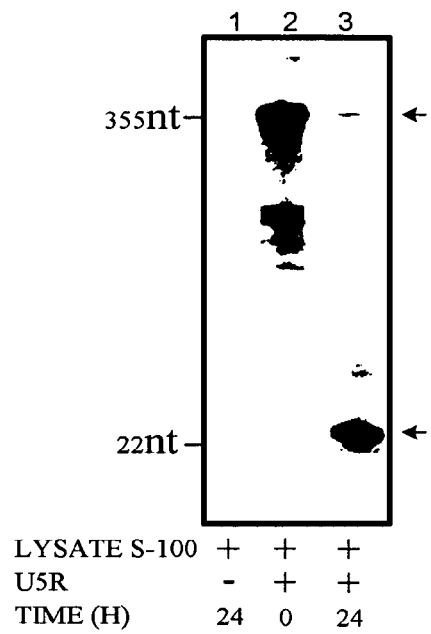

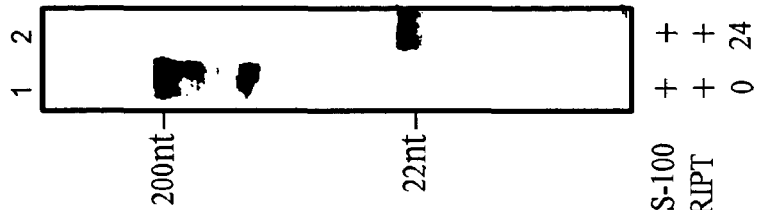

Fig 2E

TRANSCRIPT SEQUENCE (5' TO 3')

TGGGAAGCCCTCAAATATTGGTGG
AATCTCCTACAGTATTGGAGTCAG
GAACTAAAGAATAGTGCTGTTAGC
TTGCTCAATGCCACAGCCATAGCA
GTAGCTGAGGGACAGATAGGGTT
ATAGAAGTAGTACAAGGAGCTTGT
AGAGCTATTCGCCACATACCTAGA
AGAATAAGACAGGGCTTGGAAAGG
ATTTTGCT

GAM RNA:
TGAGGGGACAGATAGGGTTATAGA

LYSATE S-100    +    +
TRANSCRIPT      +    +
TIME (H)        0    24

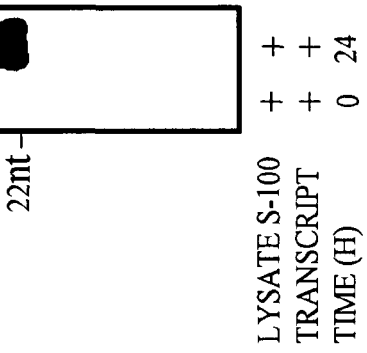

Fig 2D

TRANSCRIPT SEQUENCE (5' TO 3')

ACAGGGCTGCTATTAACAAGAGAT
GGTGGTAAATAGCAACAATGAGTCC
GAGATCTTCAGACCTGGAGGAGGA
GATATGAGGGACAATTGGAGAAGT
GAATTATATAAATATAAAGTAGTA
AAAATTGAACCATTAGGAGTAGCA
CCCACCAAGGCAAAGAGAA

GAM RNA:
TGAGTCCGAGATCTTCAGACCTGG

LYSATE S-100    +    +
TRANSCRIPT      +    +
TIME (H)        0    24

VIRAL AND VIRAL ASSOCIATED MIRNAS AND USES THEREOF

CROSS REFERENCE TO RELATED APPLICATIONS

The present application is a continuation of International Application No. PCT/IB2005/002352, filed May 26, 2005, which is a continuation-in-part of U.S. patent application Ser. No. 10/709,739, filed May 26, 2004 and which claims the benefit of U.S. Provisional Application No. 60/522,459, filed Oct. 4, 2004, U.S. Provisional Application No. 60/665, 094, filed Mar. 25, 2005, U.S. Provisional Application No. 60/522,450, filed Oct. 3, 2004, and U.S. Provisional Application No. 60/522,451, filed Oct. 3, 2004, each of which is incorporated herein by reference.

FIELD OF THE INVENTION

The invention relates in general to viral microRNA molecules and to a group of human microRNA molecules associated with viral infections, as well as various nucleic acid molecules relating thereto or derived therefrom.

BACKGROUND OF THE INVENTION

MicroRNAs (miRNAs) are short RNA oligonucleotides of approximately 22 nucleotides that are involved in gene regulation. MicroRNAs regulate gene expression by targeting mRNAs for cleavage or translational repression. Although miRNAs are present in a wide range of species including *C. elegans, Drosophila* and humans, they have only recently been identified. More importantly, the role of miRNAs in the development and progression of disease has only recently become appreciated.

As a result of their small size, miRNAs have been difficult to identify using standard methodologies. A limited number of miRNAs have been identified by extracting large quantities of RNA. MiRNAs have also been identified that contribute to the presentation of visibly discernable phenotypes. Expression array data shows that miRNAs are expressed in different developmental stages or in different tissues. The restriction of miRNAs to certain tissues or at limited developmental stages indicates that the miRNAs identified to date are likely only a small fraction of the total miRNAs.

Computational approaches have recently been developed to identify the remainder of miRNAs in the genome. Tools such as MiRscan and MiRseeker have identified miRNAs that were later experimentally confirmed. Based on these computational tools, it has been estimated that the human genome contains 200-255 miRNA genes. These estimates are based on an assumption, however, that the miRNAs remaining to be identified will have the same properties as those miRNAs already identified. Based on the fundamental importance of miRNAs in mammalian biology and disease, the art needs to identify unknown miRNAs. The present invention satisfies this need and provides a significant number of miRNAs and uses therefore. To date, no viral miRNAs have been detected.

SUMMARY OF THE INVENTION

The present invention is related to an isolated nucleic acid comprising a sequence of a pri-miRNA, pre-miRNA, miRNA, miRNA*, anti-miRNA, or a miRNA binding site, or a variant thereof. The nucleic acid may comprise SEQS: 4097721-4204913; the sequence of a precursor referred to in Table 1, 11-12 or 21-23; SEQS: 1-1142416 or 4204914-4204915; the sequence of a miRNA referred to in Table 1, 13-14 or 21-23; SEQS: 1142417-4097720; the sequence of a target gene binding site referred to in Tables 4, 10 or 15-16; a complement thereof; or a sequence comprising at least 12 contiguous nucleotides at least 70% identical thereto. The isolated nucleic acid may be from 5-250 nucleotides in length.

The present invention is also related to a probe comprising the nucleic acid. The probe may comprise at least 8-22 contiguous nucleotides complementary to SEQS: 1-1142416 or 4204914-4204915, a miRNA referred to in Table 1, 13-14 or 21-23, or a variant thereof. The probe may also comprise at least 8-22 contiguous nucleotides complementary to a human miRNA differentially expressed in viral infection, or variant thereof.

The present invention is also related to a plurality of the probes. The plurality of probes may comprise at least ten of the probes. The plurality of probes may also comprise at least 100 of the probes. The present invention is also related to a composition comprising a probe or plurality of probes. The present invention is also related to a biochip comprising a solid substrate, said substrate comprising a plurality of the probes. Each of the probes may be attached to the substrate at a spatially defined address. The biochip may comprise probes that are complementary to a viral miRNA. The biochip may also comprise probes that are complementary to a human miRNA characterized by expression during viral infection.

The present invention is also related to a method of detecting differential expression of a disease-associated miRNA. A biological sample may be provided and the level of a nucleic acid measured that is at least 70% identical to SEQS: 1-1142416 or 4204914-4204915; the sequence of a miRNA referred to in Table 1, 13-14 and 21-23; or a variant thereof. A difference in the level of the nucleic acid compared to a control is indicative of differential expression.

The present invention is also related to a method of identifying a compound that modulates a pathological condition. A cell may be provided that is capable of expressing a nucleic acid at least 70% identical to SEQS: 1-1142416; the sequence of a miRNA referred to in Table 1, 13-14 and 21-23; or a variant thereof. The cell may be contacted with a candidate modulator and then measuring the level of expression of the nucleic acid. A difference in the level of the nucleic acid compared to a control identifies the compound as a modulator of a pathological condition associated with the nucleic acid.

The present invention is also related to a method of inhibiting expression of a target gene in a cell. Into the cell, a nucleic acid may be introduced in an amount sufficient to inhibit expression of the target gene. The target gene may comprise a binding site substantially identical to a binding site referred to in Tables 4, 10 or 15-16, or a variant thereof. The nucleic acid may comprise a portion of SEQS: 1-1142416 or 4204914-4204915; the sequence of a miRNA referred to in Table 1, 13-14 or 21-23; or a variant thereof. Expression of the target gene may be inhibited in vitro or in vivo.

The present invention is also related to a method of increasing expression of a target gene in a cell. Into the cell, a nucleic acid may be introduced in an amount sufficient to increase expression of the target gene. The target gene may comprise a binding site substantially identical to a binding site referred to in Tables 4, 10 or 15-16, or a variant thereof. A portion of the nucleic acid may be substantially complementary to SEQS: 1-1142416 or 4204914-4204915; the sequence of a miRNA referred to in Table 1, 13-14 or 21-23; or a variant thereof. Expression of the target gene may be inhibited in vitro or in vivo. Expression of the target gene may be increased in vitro or in vivo.

The present invention is also related to a method of treating a patient with a disorder set forth on Table 6 comprising administering to a patient in need thereof a nucleic acid comprising a sequence of SEQ ID NOS: 1-760616; a sequence set forth on Table 10; a sequence set forth on Table 17; or a variant thereof.

The present invention is also related to a method of treating a patient with a viral infection or a condition associated with a viral infection comprising administering to a patient in need thereof a nucleic acid, wherein a portion of the nucleic acid is substantially complementary to SEQ ID NOS: 1-1142416 or 4204914-4204915; the sequence of a miRNA referred to in Table 1, 13-14 or 21-23; or a variant thereof.

BRIEF DESCRIPTION OF SEQUENCE LISTING AND TABLES

Reference is made to the sequence listing file submitted on duplicate copies of a compact disc labeled "Substitute Sequence Listing" submitted herewith. The compact disc contains the following: SL.txt (122,213 KB, Oct. 26, 2015), which is the Sequence Listing, the contents of which are incorporated by reference herein.

Reference is made to the tables submitted on duplicate copies of a compact disc labeled "Tables" submitted herewith. The compact disc contains the following: "Table 2.txt" (19 KB May 26, 2005), "Table 3.txt" (2 KB, May 26, 2005), "Table 5.txt" (74 KB. May 26, 2005), "Table 6.txt" (1 KB, May 26, 2005), "Table 7.txt" (5 KB, May 26, 2005), "Table 8.txt" (190 KB, May 26, 2005), "Table 9.txt" (1 KB, May 26, 2005), and "Table 10.txt" (211 KB, May 26, 2005), the contents of which are incorporated herein by reference. Tables 1-24 described in this application are of International Patent Application No. PCT/IB2005/002352, the contents of which are incorporated herein by reference.

hybridized with predicted mature miRNA probes. The upper arrow indicates that molecular size of the entire 355 nt U5R transcript. The predicted molecular sizes of the two GAM RNAs are 22 nt and 17 nt, respectively. The lower arrow indicates the 22 nt molecular marker. Lanes: 1—HeLa lysate; 2-U5R transcript in HeLa Lysate without incubation; and 3-U5R transcript incubated for 24 hours with HeLa lysate. FIGS. 2D and 2E present partial transcripts of HIV1 RNA (SEQ ID NOS: 547374 and 547375) reacted with predicted mature HIV1 miRNA probes (SEQ ID NOS: 547376 and 547377). In each figure, the experimental transcript sequence is shown, and the predicted mature miRNA is underlined. Northern blot analyses of miRNA precursors are presented. It is demonstrated that one miRNA precursor transcript is 163 nt and the other miRNA precursor transcript is 200 nt. The predicted molecular sizes of mature miRNA are both 24 nt. The 22nt molecular marker is indicated. Lanes 1—Transcript in HeLa lysate without incubation and 2—Transcript incubated for 24 hours with HeLa lysate.

FIG. 3 shows the results of a Northern Blot. The expression profile of GAM506333 and GAM506336 in EBV-infected (B95/8 EBV) and non-infected (pBMC) cells are presented. The expression of these miRNAs was demonstrated on a miRNA microarray hybridized with RNA from B-95/8 cell lines infected with EBV. Probes against these validated miRNA predictions were hybridized with total RNA on a Northern blot. Northern blots confirmed high expression of these two miRNAs in the infected cells on the microarray.

FIG. 4 shows validation of miRNAs expressed by EBV.

FIG. 5 shows the knockout of EBV miRNAs.

DETAILED DESCRIPTION

The present invention provides nucleotide sequences of viral and viral-associated miRNAs, precursors thereto, targets thereof and related sequences. Such nucleic acids are useful for diagnostic purposes, and also for modifying target gene expression. Other aspects of the invention will become apparent to the skilled artisan by the following description of the invention.

LENGTHY TABLES

The patent contains a lengthy table section. A copy of the table is available in electronic form from the USPTO web site (http://seqdata.uspto.gov/?pageRequest=docDetail&DocID=US09624556B2). An electronic copy of the table will also be available from the USPTO upon request and payment of the fee set forth in 37 CFR 1.19(b)(3).

BRIEF DESCRIPTION OF THE DRAWINGS

FIG. 2A shows the 5'UTR of HIV1 (U5R)(SEQ ID NO: 547373) containing two predicted miRNAs in bold. The mature miRNAs are underlined, one closer to the 5' end (FIG. 2B) and the second closer to the 3' end 9FIG. 2C). The 5'-most miRNA matches the known HIV1 RNA struture named TAR to which the TAT protein binds (Nature 1987. 330:489-93). A similar miRNA (GAM NAME 506033) was also lit up on the chip. This miRNA probe was designed based on the sequence of T-tropic HIV-1 (LAV-1), Subtype B, which is one nucleotide different from the miRNA presented in FIG. 2B. FIGS. 2B and 2C depict Northern blot analysis of miRNA oligonucleotides that are present in U5R, 1. Definitions Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. It must further be noted that the terms "and" and "or" may encompass both conjunctive and disjunctive meaning unless the context clearly dictates otherwise.

Figure 1:
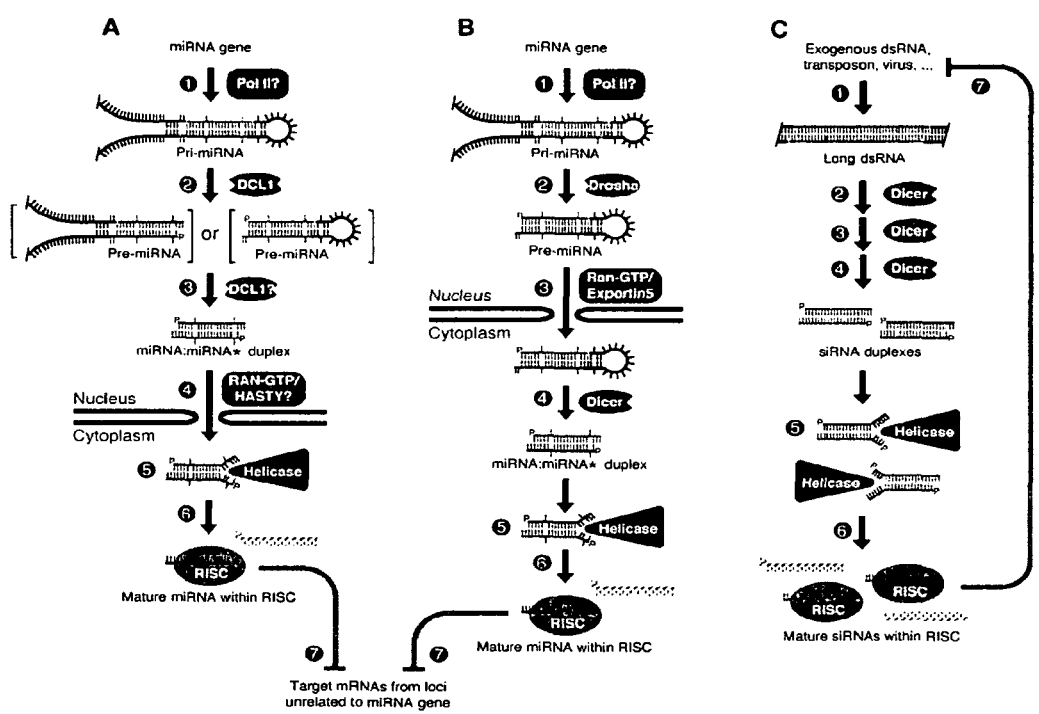
FIG. 1 demonstrates a model of maturation for miRNAs.

"Animal" as used herein may mean fish, amphibians, reptiles, birds, and mammals, such as mice, rats, rabbits, goats, cats, dogs, cows, apes and humans.

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

"Biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo. Archival tissues, such as those having treatment or outcome history, may also be used.

"Complement" or "complementary" as used herein may mean Watson-Crick or Hoogsteen base pairing between nucleotides or nucleotide analogs of nucleic acid molecules.

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type which may be detectable by standard techniques. Some genes will be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

"Gene" used herein may be a genomic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA and antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

"Host cell" used herein may be a naturally occurring cell or a transformed cell that contains a vector and supports the replication of the vector. Host cells may be cultured cells, explants, cells in vivo, and the like. Host cells may be prokaryotic cells such as E. coli, or eukaryotic cells such as yeast, insect, amphibian, or mammalian cells, such as CHO, HeLa.

"Identical" or "identity" as used herein in the context of two or more nucleic acids or polypeptide sequences, may mean that the sequences have a specified percentage of nucleotides or amino acids that are the same over a specified region. The percentage may be calculated by comparing optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces staggered end and the specified region of comparison includes only a single sequence, the residues of single sequence are included in the denominator but not the numerator of the calculation. When comparing DNA and RNA, thymine (T) and uracil (U) are considered equivalent. Identity may be performed manually or by using computer sequence algorithm such as BLAST or BLAST 2.0.

"Inhibit" as used herein may mean prevent, suppress, repress, reduce or eliminate.

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

"Nucleic acid" or "oligonucleotide" or "polynucleotide" used herein may mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid may be used for the same purpose as a given nucleic acid. Thus, a nucleic acid also encompasses substantially identical nucleic acids and complements thereof. As will also be appreciated by those in the art, a single strand provides a probe for a probe that may hybridize to the target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methyl-phosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modifications of the ribose-phosphate backbone may be done for a variety of reasons, e.g., to increase the stability and half-life of such molecules in physiological environments or as probes on a biochip. Mixtures of naturally occurring nucleic acids and analogs may be made; alternatively, mixtures of different nucleic acid analogs, and mixtures of naturally occurring nucleic acids and analogs may be made.

"Operably linked" used herein may mean that expression of a gene is under the control of a promoter with which it is spatially connected. A promoter may be positioned 5' (upstream) or 3' (downstream) of the gene under its control. The distance between the promoter and the gene may be approximately the same as the distance between that promoter and the gene it controls in the gene from which the promoter is derived. As is known in the art, variation in this distance can be accommodated without loss of promoter function.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Promoter" as used herein may mean a synthetic or naturally-derived molecule which is capable of conferring, activating or enhancing expression of a nucleic acid in a cell. A promoter may comprise one or more specific regulatory elements to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Selectable marker" used herein may mean any gene which confers a phenotype on a cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein-encoding gene and luciferase gene.

"Stringent hybridization conditions" used herein may mean conditions under which a first nucleic acid sequence (e.g., probe) will hybridize to a second nucleic acid sequence (e.g., target), such as in a complex mixture of nucleic acids, but to no other sequences. Stringent conditions are sequence-dependent and will be different in different circumstances. Generally, stringent conditions are selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence.

"Target" as used herein may mean a polynucleotide that may be bound by one or more probes under stringent hybridization conditions.

"Terminator" used herein may mean a sequence at the end of a transcriptional unit which signals termination of transcription. A terminator may be a 3'-non-translated DNA sequence containing a polyadenylation signal, which may facilitate the addition of polyadenylate sequences to the 3'-end of a primary transcript. A terminator may be derived from sources including viral, bacterial, fungal, plants, insects, and animals. Representative examples of terminators include the SV40 polyadenylation signal, HSV TK polyadenylation signal, CYC1 terminator, ADH terminator, SPA terminator, nopaline synthase (NOS) gene terminator of *Agrobacterium tumefaciens*, the terminator of the *Cauliflower mosaic virus* (CaMV) 35S gene, the zein gene terminator from *Zea mays*, the Rubisco small subunit gene (SSU) gene terminator sequences, subclover stunt virus (SCSV) gene sequence terminators, rho-independent *E. coli* terminators, and the lacZ alpha terminator.

"Treat" or "treating" used herein when referring to protection of an animal from a condition, means preventing, suppressing, repressing, or eliminating the condition. Preventing the condition involves administering a composition of the present invention to an animal prior to onset of the condition. Suppressing the condition involves administering a composition of the present invention to an animal after induction of the condition but before its clinical appearance. Repressing the condition involves administering a composition of the present invention to an animal after clinical appearance of the condition such that the condition is reduced or prevented from worsening. Elimination of the condition involves administering a composition of the present invention to an animal after clinical appearance of the condition such that the animal no longer suffers from the condition.

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. MicroRNA

While not being bound by theory, the current model for the maturation of mammalian miRNAs is shown in FIG. 1. A gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. As indicated on FIG. 1, the stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as single-stranded RNAs into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke at al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA complementarity sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity.

It should be notes that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. Nucleic Acid

The present invention relates to an isolated nucleic acid comprising a nucleotide sequence referred to in SEQS: 1-4204915, the sequences referred to in Tables 1, 4, 10-14 and 21-23, and variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 100 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80 or 90 nucleotides. The nucleic acid may be synthesized or expressed in a cell (in vitro or in vivo) using a synthetic gene described below. The nucleic acid may be synthesized as a single strand molecule and hybridized to a substantially complementary nucleic acid to form a duplex, which is considered a nucleic acid of the invention. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

a. Pri-MiRNA

The nucleic acid of the invention may comprise a sequence of a pri-miRNA or a variant thereof. The pri-miRNA sequence may comprise from 45-250, 55-200, 70-150 or 80-100 nucleotides. The sequence of the pri-miRNA may comprise a pre-miRNA, miRNA and miRNA* as set forth below. The pri-miRNA may also comprise a miRNA or miRNA* and the complement thereof, and variants thereof. The pri-miRNA may comprise at least 19% adenosine nucleotides, at least 16% cytosine nucleotides, at least 23% thymine nucleotides and at least 19% guanine nucleotides.

The pri-miRNA may form a hairpin structure. The hairpin may comprise a first and second nucleic acid sequence that are substantially complementary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides.

The sequence of the pri-miRNA may comprise SEQS: 4097721-4204913, a precursor referred to in Table 1, the sequence of a sequence referred to in Tables 11-12 and 21-23, or a variant thereof.

b. Pre-MiRNA

The nucleic acid of the invention may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth below. The pre-miRNA may also comprise a miRNA or miRNA* and the complement thereof, and variants thereof. The sequence of the pre-miRNA may also be that of a pri-miRNA excluding from 0-160 nucleotides from the 5' and 3' ends of the pri-miRNA.

The sequence of the pre-miRNA may comprise SEQS: 4097721-4204913, a precursor referred to in Table 1, the sequence of a sequence referred to in Tables 11-12 and 21-23, or a variant thereof.

c. MiRNA

The nucleic acid of the invention may also comprise a sequence of a miRNA, miRNA* or a variant thereof. The miRNA sequence may comprise from 13-33, 18-24 or 21-23 nucleotides. The sequence of the miRNA may be the first 13-33 nucleotides of the pre-miRNA. The sequence of the miRNA may be the last 13-33 nucleotides of the pre-miRNA.

The sequence of the miRNA may comprise SEQS: 1-1142416 or 4204914-4204915, a miRNA referred to in Table 1, the sequence of a sequence referred to in Tables 11-12 and 21-23, or a variant thereof.

d. Anti-MiRNA

The nucleic acid of the invention may also comprise a sequence of an anti-miRNA that is capable of blocking the activity of a miRNA or miRNA*. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25 or 26 nucleotides. The sequence of the anti-miRNA may comprise (a) at least 5 nucleotides that are substantially identical to the 5' of a miRNA and at least 5-12 nucleotide that are substantially complementary to the flanking regions of the target site from the 5' end of said miRNA, or (b) at least 5-12 nucleotides that are substantially identical to the 3' of a miRNA and at least 5 nucleotide that are substantially complementary to the flanking region of the target site from the 3' end of said miRNA.

The sequence of the anti-miRNA may comprise the complement of SEQS: 1-1142416 or 4204914-4204915, a sequence of a miRNA referred to in Tables 1, 13-14 or 21-23, or a variant thereof.

e. Binding Site of Target

The nucleic acid of the invention may also comprise a sequence of a target miRNA binding site, or a variant thereof. The target site sequence may comprise a total of 5-100 or 10-60 nucleotides. The target site sequence may comprise at least 5 nucleotides of SEQS: 1142417-4097720, the sequence of a target gene binding site referred to in Tables 4, 10 or 15-16, or a variant thereof.

4. Synthetic Gene

The present invention also relates to a synthetic gene comprising a nucleic acid of the invention operably linked to a transcriptional and/or translational regulatory sequences.

The synthetic gene may be capable of modifying the expression of a target gene with a binding site for the nucleic acid of the invention. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. Vector

The present invention also relates to a vector comprising a synthetic gene of the invention. The vector may be an expression vector. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. Host Cell

The present invention also relates to a host cell comprising a vector of the invention. The cell may be a bacterial, fungal, plant, insect or animal cell.

7. Probes

The present invention also relates to a probe comprising a nucleic acid of the invention. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

8. Biochip

The present invention also relates to a biochip. The biochip may comprise a solid substrate comprising an attached probe or plurality of probes of the invention. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder.

The probes may be attached to the biochip in a wide variety of ways, as will be appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. MiRNA Expression Analysis

The present invention also relates to a method of identifying miRNAs that are associated with disease or a pathological condition, such as viral infection, comprising contacting a biological sample with a probe or biochip of the invention and detecting the amount of hybridization. PCR may be used to amplify nucleic acids in the sample, which may provide higher sensitivity.

The ability to identify miRNAs that are overexpressed or underexpressed in pathological cells compared to a control can provide high-resolution, high-sensitivity datasets which may be used in the areas of diagnostics, therapeutics, drug development, pharmacogenetics, biosensor development, and other related areas. An expression profile generated by the current methods may be a "fingerprint" of the state of the sample with respect to a number of miRNAs. While two states may have any particular miRNA similarly expressed, the evaluation of a number of miRNAs simultaneously allows the generation of a gene expression profile that is characteristic of the state of the cell. That is, normal tissue may be distinguished from diseased tissue. By comparing expression profiles of tissue in known different disease states, information regarding which miRNAs are associated in each of these states may be obtained. Then, diagnosis may be performed or confirmed to determine whether a tissue sample has the expression profile of normal or disease tissue. This may provide for molecular diagnosis of related conditions.

10. Determining Expression Levels

The present invention also relates to a method of determining the expression level of a disease-associated miRNA comprising contacting a biological sample with a probe or biochip of the invention and measuring the amount of hybridization. The expression level of a disease-associated miRNA is information in a number of ways. For example, a differential expression of a disease-associated miRNA compared to a control may be used as a diagnostic that a patient suffers from the disease. Expression levels of a disease-associated miRNA may also be used to monitor the treatment and disease state of a patient. Furthermore, expression levels of a disease-associated miRNA may allow the screening of drug candidates for altering a particular expression profile or suppressing an expression profile associated with disease.

A target nucleic acid may be detected by contacting a sample comprising the target nucleic acid with a biochip comprising an attached probe sufficiently complementary to the target nucleic acid and detecting hybridization to the probe above control levels.

The target nucleic acid may also be detected by immobilizing the nucleic acid to be examined on a solid support such as nylon membranes and hybridizing a labeled probe with the sample. Similarly, the target nucleic may also be detected by immobilizing the labeled probe to the solid support and hybridizing a sample comprising a labeled target nucleic acid. Following washing to remove the non-specific hybridization, the label may be detected.

The target nucleic acid may also be detected in situ by contacting permeabilized cells or tissue samples with a labeled probe to allow hybridization with the target nucleic acid. Following washing to remove the non-specifically bound probe, the label may be detected.

These assays can be direct hybridization assays or can comprise sandwich assays, which include the use of multiple probes, as generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference.

A variety of hybridization conditions may be used, including high, moderate and low stringency conditions as outlined above. The assays may be performed under stringency conditions which allow hybridization of the probe only to the target. Stringency can be controlled by altering a step parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

a. Diagnostic

The present invention also relates to a method of diagnosis comprising detecting a differential expression level of a disease- or infection-associated miRNA in a biological sample. The miRNA may be a viral miRNA, which may be expressed in the infected subject. The miRNA may also be from the subject, the expression level of which is modified due to a viral infection. The sample may be derived from a patient. Diagnosis of a disease state in a patient allows for prognosis and selection of therapeutic strategy. Further, the developmental stage of cells may be classified by determining temporarily expressed miRNA-molecules.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

b. Drug Screening

The present invention also relates to a method of screening therapeutics comprising contacting a pathological cell capable of expressing a disease related miRNA with a candidate therapeutic and evaluating the effect of a drug candidate on the expression profile of the disease associated miRNA. Having identified the differentially expressed miRNAs, a variety of assays may be executed. Test compounds may be screened for the ability to modulate gene expression of the disease associated miRNA. Modulation includes both an increase and a decrease in gene expression.

The test compound or drug candidate may be any molecule, e.g., protein, oligopeptide, small organic molecule, polysaccharide, polynucleotide, etc., to be tested for the capacity to directly or indirectly alter the disease phenotype or the expression of the disease associated miRNA. Drug candidates encompass numerous chemical classes, such as small organic molecules having a molecular weight of more than 100 and less than about 500, 1,000, 1,500, 2,000 or 2,500 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Combinatorial libraries of potential modulators may be screened for the ability to bind to the disease associated miRNA or to modulate the activity thereof. The combinatorial library may be a collection of diverse chemical compounds generated by either chemical synthesis or biological synthesis by combining a number of chemical building blocks such as reagents. Preparation and screening of combinatorial chemical libraries is well known to those of skill in the art. Such combinatorial chemical libraries include, but are not limited to, peptide libraries encoded peptides, benzodiazepines, diversomers such as hydantoins, benzodiazepines and dipeptide, vinylogous polypeptides, analogous organic syntheses of small compound libraries, oligocarbamates, and/or peptidyl phosphonates, nucleic acid libraries, peptide nucleic acid libraries, antibody libraries, carbohydrate libraries, and small organic molecule libraries.

11. Gene Silencing

The present invention also relates to a method of using the nucleic acids of the invention to reduce expression of a target gene in a cell, tissue or organ. Expression of the target gene may be reduced by expressing a nucleic acid of the invention that comprises a sequence substantially complementary to one or more binding sites of the target mRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target mRNA, which may lead to activation of RISC-mediated gene silencing. An example for a study employing over-expression of miRNA is Yekta et al 2004, Science 304-594, which is incorporated herein by reference. One of ordinary skill in the art will recognize that the nucleic acids of the present invention may be used to inhibit expression of target genes using antisense methods well known in the art, as well as RNAi methods described in U.S. Pat. Nos. 6,506,559 and 6,573,099, which are incorporated by reference.

The target gene may be a viral gene, which may be reduced by expressing a viral or human miRNA. The target gene may also be a human gene that is expressed upon viral infection, which may be reduced by expressing a viral or human miRNA. The target of gene silencing may be a protein that causes the silencing of a second protein. By repressing expression of the target gene, expression of the second protein may be increased. Examples for efficient suppression of miRNA expression are the studies by Esau et al 2004 JBC 275-52361; and Cheng et al 2005 Nucleic Acids Res. 33-1290, which is incorporated herein by reference.

12. Gene Enhancement

The present invention also relates to a method of using the nucleic acids of the invention to increase expression of a target gene in a cell, tissue or organ. Expression of the target gene may be increased by expressing a nucleic acid of the invention that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target gene may also be increased by expressing a nucleic acid of the invention that is substantially complementary to a portion of the binding site in the target gene, such that binding of the nucleic acid to the binding site may prevent miRNA binding.

The target gene may be a viral gene, expression of which may reduce infectivity of the virus. The target gene may also be a human gene, expression of which may reduce infectivity of the virus or increase resistance or immunity to the viral infection.

13. Therapeutic

The present invention also relates to a method of using the nucleic acids of the invention as modulators or targets of disease or disorders, such as those associated with viral infection. In general, the claimed nucleic acid molecules may be used as a modulator of the expression of genes which are at least partially complementary to said nucleic acid. Further, miRNA molecules may act as target for therapeutic screening procedures, e.g. inhibition or activation of miRNA molecules might modulate a cellular differentiation process, e.g. apoptosis.

Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. Further, miRNA molecules can be modified, in order that they are processed and then generated as double-stranded siRNAs which are again directed against therapeutically relevant targets. Furthermore, miRNA molecules may be used for tissue reprogramming procedures, e.g. a differentiated cell line might be transformed by expression of miRNA molecules into a different cell type or a stem cell.

14. Compositions

The present invention also relates to a pharmaceutical composition comprising the nucleic acids of the invention and optionally a pharmaceutically acceptable carrier. The compositions may be used for diagnostic or therapeutic applications. The administration of the pharmaceutical composition may be carried out by known methods, wherein a nucleic acid is introduced into a desired target cell in vitro or in vivo. Commonly used gene transfer techniques include calcium phosphate, DEAE-dextran, electroporation, microinjection, viral methods and cationic liposomes.

15. Kits

The present invention also relates to kits comprising a nucleic acid of the invention together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods of this invention.

Example 1

Prediction of MiRNAs

We surveyed a number of viral genomes for potential miRNA coding genes using three computational approaches similar to those described in U.S. Patent Application No. 60/522,459, Ser. Nos. 10/709,577 and 10/709,572, the contents of which are incorporated herein by reference, for predicting miRNAs. The predicted hairpins and potential miRNAs were scored by thermodynamic stability, as well as structural and contextual features. The algorithm was calibrated by using miRNAs in the Sanger Database which had been validated.

1. First and Second Screen

Tables 11 and 12 show the sequence ("PRECURSOR SEQUENCE"), sequence identifier ("PRECUR SEQ-ID") and organism of origin ("GAM ORGANISM") for each predicted hairpin from the first computational screen, together with the predicted miRNAs ("GAM NAME"). Tables 13 and 14 show the sequence ("GAM RNA SEQUENCE") and sequence identifier ("GAM SEQ-ID") for each miRNA ("GAM NAME"), along with the organism of origin ("GAM ORGANISM") and Dicer cut location ("GAM POS").

2. Third Screen

Table 1 lists the SEQ ID NO for each predicted hairpin ("HID") of the third computational screen of a particular viral genome ("V"; See also Table 10). Table 1 also lists the genomic location for each hairpin ("Hairpin Location"). The format for the genomic location is a concatenation of <strand><start position>. The genetic location is based on the NCBI—Entrez Nucleotides database. The Entrez Nucleotides database is a collection of sequences from several sources, including GenBank, RefSeq, and PDB. Table 10 shows the accession number and the build (version) are presented for each of the genomes used in this screen.

Table 1 also lists the SEQ ID NO ("MID") for each predicted miRNA and miRNA*. Table 1 also lists the prediction score grade for each hairpin ("P") on a scale of 0-1 (1 the hairpin is the most reliable), as described in Hofacker et al., Monatshefte f. Chemie 125: 167-188, 1994. Table 1 also lists the p-value ("Pval") calculated out of background hairpins for the values of each P scores. All the p-values are significant—lower than 0.05. As shown in Table 1, there are few instances where the Pval is 0.0. In each of these cases, the value is less than 0.0001. The p-values were calculated by comparing the palgrade of the tested hairpin to the palgrade of other sequences without pre-selection of hairpins.

Table 1 also lists whether the miRNAs were validated by expression analysis ("E") (Y=Yes, N=No), as detailed in Table 2. Table 1 also lists whether the miRNAs were validated by sequencing ("S") (Y=Yes, N=No), as detailed in Table 3. If there was a difference in sequences between the predicted and sequenced miRNAs, the sequenced sequence is presented. It should be noted that failure to sequence or detect expression of a miRNA does not necessarily mean that a miRNA does not exist. Such undetected miRNAs may be expressed in tissues other than those tested. In addition, such undetected miRNAs may be expressed in the test tissues, but at a difference stage or under different condition than those of the experimental cells.

Table 1 also listed whether the miRNAs were shown to be differentially expressed ("D") (Y=Yes, N=No) in at least one disease, as detailed in Table 2). Table 1 also whether the miRNAs were present ("F") (Y=Yes, N=No) in Sanger D B Release 6.0 (April 2005) (http://nar.oupjournals.org/) as being detected in humans or mice or predicted in humans. As discussed above, the miRNAs listed in the Sanger database are a component of the prediction algorithm and a control for the output.

Table 1 also lists a genetic location cluster ("LC") for those hairpins that are within 1,000 nucleotides of each other of a particular virus. Each miRNA that has the same LC share the same genetic cluster. Those hairpins that overlap are not clustered. Table 1 also lists a seed cluster ("SC") to group miRNAs by their seed of 2-7 by an exact match, regardless of the source virus. Each miRNA that has the same SC have the same seed. For a discussion of seed lengths of 6 nucleotides, see Lewis et al., Cell, 120;15-20 (2005).

Example 2

Prediction of Target Genes

The predicted miRNAs from the three computational screens of Example 1 were then used to predict human and viral target genes and their binding sites using two computational approaches similar to those described in U.S. Patent Application No. 60/522,459, Ser. Nos. 10/709,577 and 10/709,572, the contents of which are incorporated herein by reference, for predicting miRNAs.

1. First and Second Screen

Tables 15 and 16 list the predicted target genes ("TARGET") and binding site sequence ("TARGET BINDING SITE SEQUENCE") and binding site sequence identifier ("TARGET BINDING SITE SEQ-ID") from the first computational screen, as well as the organism of origin for the target ("TARGET ORGANISM").

2. Third Screen a. Human Target Genes

Table 4 lists the predicted human target gene for each miRNA (MID) from a particular virus (V) and its hairpin (HID) from the third computational screen. The names of the target genes were taken from NCBI Reference Sequence release 9 (http://www.ncbi.nlm.nih.gov; Pruitt et al., Nucleic Acids Res, 33(1):D501-D504, 2005; Pruitt et al., Trends Genet., 16(1):44-47, 2000; and Tatusova et al., Bioinformatics, 15(7-8):536-43, 1999). Target genes were identified by having a perfect complementary match of a 7 nucleotide miRNA seed (positions 2-8) and an A on the UTR (total=8 nucleotides). For a discussion on identifying target genes, see Lewis et al., Cell, 120: 15-20, (2005). For a discussion of the seed being sufficient for binding of a miRNA to a UTR, see Lim Lau et al., (Nature 2005) and Brenneck et al, (PLoS Biol 2005).

The binding site screen only considered the first 4000 nucleotides per UTR and considered the longest transcript when there were several transcripts per gene. The filtering reduced the total number of transcripts from 23626 to 14239. Table 4 lists the SEQ ID NO for the predicted binding sites for each target gene. The sequence of the binding site includes the 20 nucleotides 5' and 3' of the binding site as they are located on the spliced mRNA. In cases that the binding site is comprised from 2 exons, 20 nucleotides are included from both 5' and 3' ends of both exons.

Table 5 shows the relationship between the miRNAs ("MID")/hairpins ("HID") of a particular virus ("V") and diseases by their human target genes. The name of the diseases are taken from OMIM. For a discussion of the rationale for connecting the host gene the hairpin is located upon to disease, see Baskerville and Bartel, RNA, 11: 241-247 (2005) and Rodriguez et al., Genome Res., 14: 1902-1910 (2004). Table 5 shows the number of miRNA target genes ("N") that are related to the disease. Table 5 also shows the total number of genes that are related to the disease ("T"), which is taken from the genes that were predicted to have binding sites for miRNAs. Table 5 also shows the percentage of N out of T and the p-value of hypergeometric analysis ("Pval"). In cases that the pval is listed as 0.0, it means that the value is less than 0.0001. For a reference of hypergeometric analysis, see Schaum's Outline of Elements of Statistics II: Inferential Statistics. Table 7 shows the disease codes for Tables 5 and 6.

b. Viral Target Genes

Similar to the date described above in Table 4 for human target genes, Table 10 lists the predicted viral target gene for each miRNA (MID) from the same particular virus (V) and its hairpin (HID) from the third computational screen. The prediction of viral binding sites used complete genes not UTRs as in the Table 4 in the method described above for human target genes Table 10. Candidate target genes were included in the screen if they were known to have a role in the virus life cycle. Those miRNAs that have binding sites on a viral gene that takes part in the virus life cycle they may affect the diseases that may be related to the virus Human Herpes virus 1 and 2 are related to any of several inflammatory diseases caused by a herpesvirus and marked in one case by groups of watery blisters on the skin or mucous membranes (as of the mouth and lips) above the waist and in the other by such blisters on the genitals. *Human herpesvirus* 4 (Epstein-Barr virus) causes infectious mononucleosis and is associated with Burkitt's lymphoma and nasopharyngeal carcinoma. HIV strains are related to Acquired Immune Deficiency Syndrome (AIDS). Hepatitis B and C viruses cause inflammation of the liver.

Example 3

Validation of MiRNAs

To confirm the hairpins and miRNAs predicted in Example 1, we detected expression in various tissues using the high-throughput microarrays similar to those described in U.S. Patent Application No. 60/522,459, Ser Nos. 10/709, 577 and 10/709,572, the contents of which are incorporated herein by reference. For each predicted precursor miRNA, mature miRNAs derived from both stems of the hairpin were tested.

1. Expression Analysis—Set 1 and Set 2

Tables 17-19 list the results of microarray expression analysis to detch miRNA sequence ("GAM RNA SEQUENCE").

2. Expression Analysis—Set 3

Table 2 shows the hairpins ("HID") of the third prediction set that were validated by detecting expression of related miRNAs ("MID") from a particular virus ("V"), as well as a code for the tissue ("Tissue") that expression was detected.

In cases where there is more than one score from the same miRNA in the same tissue, only the one with the higher score is presented.

The tissue and diseases codes are listed in Table 6 and Table 7, respectively. Table 8 shows the relationship between gene and disease. This enables the connection of all miRNAs to disease. Table 4 assign at least one target gene to each miRNA. Table 5 presents the outcome of statistical analysis of table 4 and OMIM to depict significant relations of miRNAs and disease. Table 8 is basically a condensed version of OMIM. It lists for each gene all the numeric codes of the diseases that are related to it.

All the tissues disclosed give an indication of a viral disease. The fact that significant expression of the virus was measured implies that in this tissue it may be involve in a viral disease(s). E.g. when a mir from HIV was expressed in T cell line it may have an effect on AIDS. Of course cell lines represent only subset of the features of a tissue as it function in an organ however we can deduce from the expression as it is measured in the cell line.

Table 2 also shows the chip expression score grade (range of 500-65000) ("S"). A threshold of 500 was used to eliminate non-significant signals and the score was normalized by MirChip probe signals from different experiments. Variations in the intensities of fluorescence material between experiments may be due to variability in RNA preparation or labeling efficiency. We normalized based on the assumption that the total amount of miRNAs in each sample is relatively constant. First we subtracted the background signal from the raw signal of each probe, where the background signal is defined as 400. Next, we divided each miRNA probe signal by the average signal of all miRNAs, multiplied the result by 10000 and added back the background signal of 400. Thus, by definition, the sum of all miRNA probe signals in each experiment is 10400.

Table 2 also shows a statistical analysis of the normalized signal ("Spval") calculated on the normalized score. For each miRNA, we used a relevant control group out of the full predicted miRNA list. Each miRNA has an internal control of probes with mismatches. The relevant control group contained probes with similar C and G percentage (abs diff <5%) in order to have similar Tm. The probe signal P value is the ratio over the relevant control group probes with the same or higher signals. The results are p-value ≤0.05 and score is above 500. In those cases that the SPVal is listed as 0.0, the value is less than 0.0001.

3. Sequencing—Set 3

To further validate the hairpins ("HID") of the second prediction, a number of miRNAs were validated by sequencing methods similar to those described in U.S. Patent Application No. 60/522,459, Ser. Nos. 10/709,577 and 10/709,572, the contents of which are incorporated herein by reference. Table 3 shows the hairpins ("HID") that were validated by sequencing a miRNA (MID) from a virus ("V") in the indicated tissue ("Tissue").

4. Northern Analysis

Figure 3:
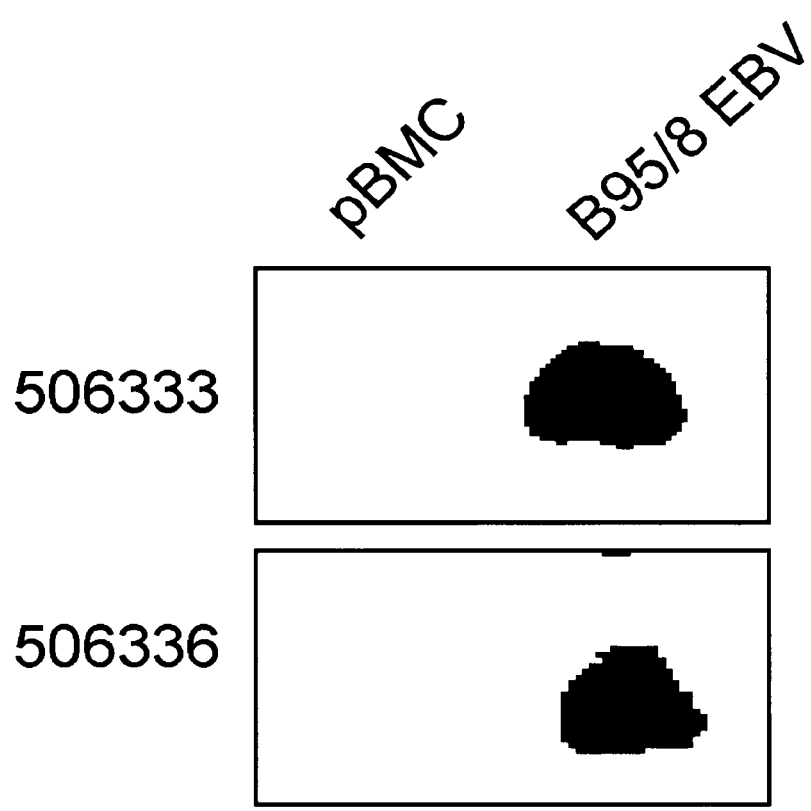

A group of miRNA were validated by Northern analysis, as shown in FIGS. 2 and 3.

Example 4

Differential Expression of MiRNAs

1. Viral MiRNAs

Table 20 provides validated viral miRNAs that were demonstrated to be differentially expressed in diseased compared to healthy human tissue or human-derived cell lines. All miRNA sequences were validated using a miRNA microarray as described hereinabove. For Alzheimer Disease, GAM RNA expression was studied in a mixture of tissue from diseased and healthy human amygdala, cingulate cortex, caudate nucleus, globus pallidus, posterior parietal cortex, and superior parietal cortex, all brain regions that were shown to be affected mildly, moderately, or severely by Alzheimer pathology. For Parkinson Disease, GAM RNA expression was studied in substantia nigra tissue from diseased and healthy human tissue. MT2 cell lines were infected with a T-tropic clinical isolation of Clade A Human Immunodeficiency Virus (HIV), while healthy controls were not infected. cMagi cell lines were infected with a M-tropic Clade B HIV, while healthy controls were not infected. Human fibroblast cells (TC) were infected with HSV1 or HSV2 or were not infected and served as controls. GAM RNA SEQUENCE: the sequence (5' to 3') of the mature, "diced" GAM RNA. CHIP SEQUENCE is the sequence of the oligonucleotide including the predicted GAM RNA that was placed on the microarray (not including the non-genomic sequence used as a separator from the microarray surface). DISEASE: the disease in which the GAM RNA was differentially expressed—BAL refers to M-tropic HIV1 Subtype B, lab strain, and BLAI refers to T-tropic HIV-1 (LAV-1), Subtype B; SIGNAL (HEALTHY): the signal on the microarray for the GAM RNA in samples comprised of human tissue or human-derived cell lines that are not afflicted with the specified disease; SIGNAL (DISEASE): the signal on the microarray for the GAM RNA in samples comprised of human tissue or human-derived cell lines that are afflicted with the specified disease.

2. Human MiRNAs

Table 21 lists expression data of miRNAs by the following: HID: hairpin SEQ; MID: MiRNA SEQ; Tissue: tested tissue; S: chip expression score grade (range=100-65000); Dis. Diff. Exp.: disease related differential expression and the tissue it was tested in; R: ratio of disease related expression (range=0.01-99.99); and abbreviations: Brain Mix A—a mixture of brain tissue that are affected in Alzheimer; Brain Mix B—a mixture of all brain tissues; and Brain SN—Substantia Nigra. Tables 22 and 23 provide the details regarding the differentially expressed miRNAs by the following: HID: hairpin SEQ; Hairpin_Loc: hairpin genomic hocation, concatenating <chr_id><strand>space<start position> (e.g., 19+135460000 means chr19+strand, start position 135460000); C: conservation in evolution (Yes/No and "—" when data is not available; Yes—conservation level above threshold of 0.7); T: genomic type, InterGenic (G), Intron (I), Exon (E); MID: MiRNA SEQ; Target Gene, Disease: target gene (HUGO database) and related disease (OMIM database); P: prediction score grade, on range 0-9; E: chip expression information—Yes/No (Y/N); S: validation by eequencing—Yes/No (Y/N); HID: hairpin SEQ. Table 24 provides the sequence for the sequences referred to in Tables 21-23.

Example 4

Analysis of EBV MiRNAs

1. Validation of Expression

Figure 4:
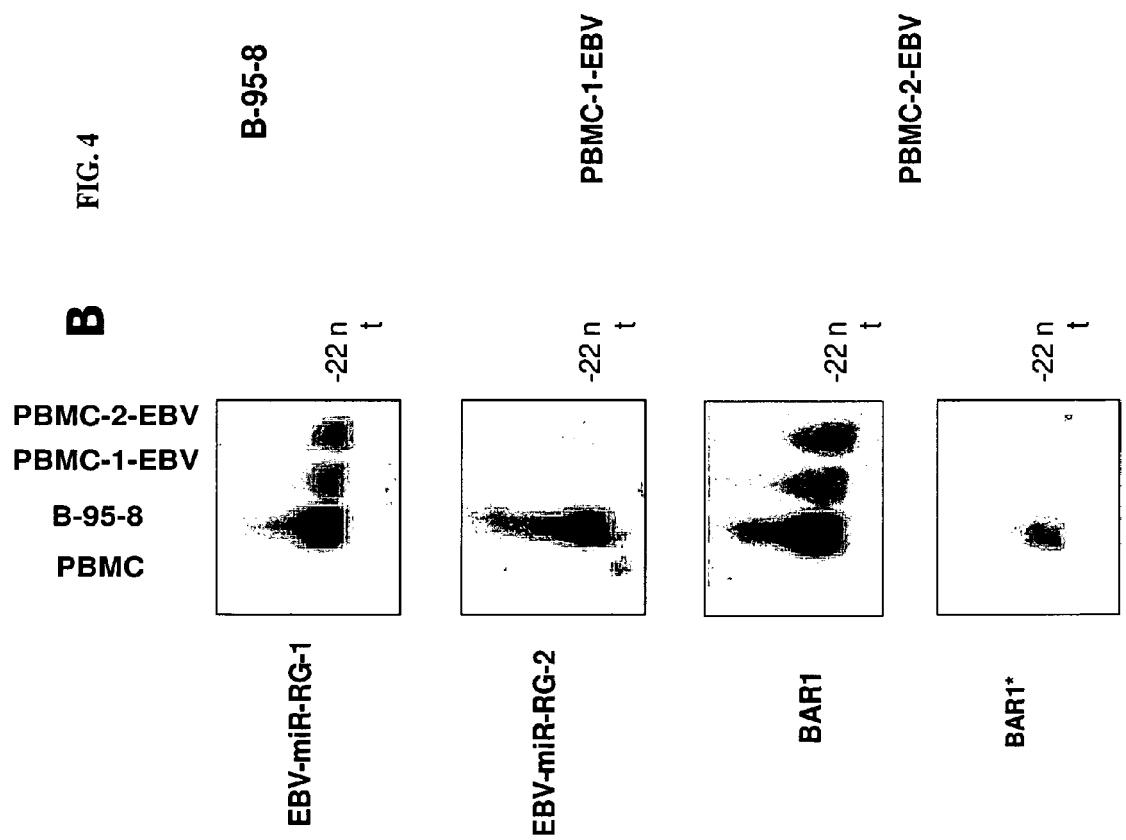

FIG. 4 shows the validation of expression of miRNAs predicted in EBV (Epstein's Barr Virus) miRNAs; expression validation. Three cell line were tested. Two were freshly infected normal B-cells (PBMC-1/2-EBV), and one EBV-transformed cell line (B-95-8). The 3 cell lines exhibit the same extent of EBV infection (FIG. 4A). However, in contrast to the freshly infected B cells, EBV-miR-RG-1 and -2 are highly expressed in the B-95-8 cell-line (FIG. 4B).

2. Knockout of Expression

Figure 5:
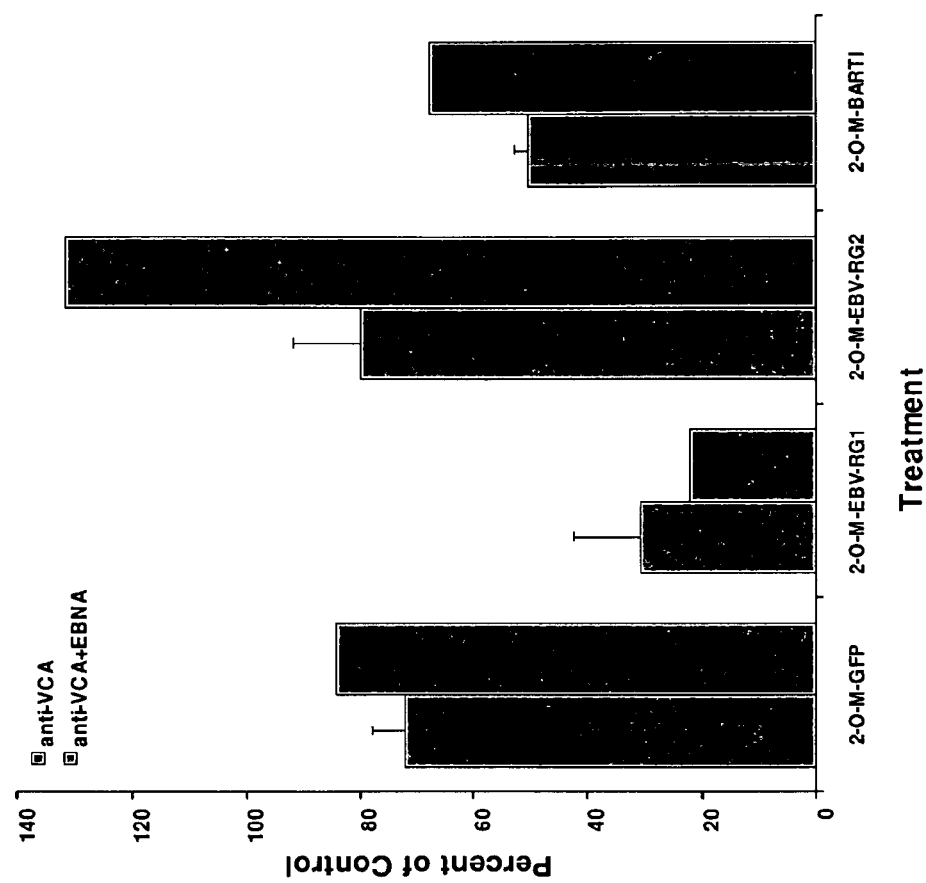

FIG. 5 shows the knockout of EBV miRNAs. Addition of 2-O-Methyl against EBV-miR-RG-1 to B-95-8 cell line resulted is dramatic reduction of cells expressing EBV antigens. Addition of 2-O-Methyl against EBV-miR-RG-2 to B-95-8, had a moderate effect, slightly increasing EBV expression.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09624556B2). An electronic copy of the "Sequence Listing" will also be available from the USPTO upon request and payment of the fee set forth in 37 CFR 1.19(b)(3).

The invention claimed is:

1. A nucleic acid selected from the group consisting of:
   (a) the sequence of SEQ ID NO: 2015;
   (b) a DNA encoding the sequence of (a), wherein the DNA is identical in length to (a);
   (c) a sequence at least 95% identical to (a) or (b); and
   (d) the complement of one of the nucleic acids of (a)-(c), wherein the complement is identical in length to the one of the nucleic acids of (a)-(c);
   wherein the nucleic acid comprises a non-naturally occurring nucleotide.

2. A probe comprising a heterologous sequence, wherein the heterologous sequence consists of a nucleic acid sequence selected from the group consisting of:
   (a) the sequence of SEQ ID NO: 2015;
   (b) a DNA encoding the sequence of (a), wherein the DNA is identical in length to (a);
   (c) a sequence at least 95% identical to (a) or (b); and
   (d) the complement of one of the nucleic acids of (a)-(c), wherein the complement is identical in length to the one of the nucleic acids of (a)-(c).

3. The probe of claim 2, wherein the probe comprises at least one of a non-naturally occurring nucleotide and a label.

4. The probe of claim 2, wherein the probe is attached to a solid substrate.

5. The probe of claim 4, wherein the solid substrate is a biochip.

6. A vector comprising a heterologous sequence, wherein the heterologous sequence consists of a nucleic acid sequence selected from the group consisting of:
   (a) the sequence of SEQ ID NO: 2015;
   (b) a DNA encoding the sequence of (a), wherein the DNA is identical in length to (a);
   (c) a sequence at least 95% identical to (a) or (b); and
   (d) the complement of one of the nucleic acids of (a)-(c), wherein the complement is identical in length to the one of the nucleic acids of (a)-(c).

\* \* \* \* \*